(12) United States Patent
Sun

(10) Patent No.: US 11,565,987 B2
(45) Date of Patent: Jan. 31, 2023

(54) COMPOSITIONS AND PROCESSES FOR PRODUCING CHLOROFLUOROALKENES

(71) Applicant: THE CHEMOURS COMPANY FC, LLC, Wilmington, DE (US)

(72) Inventor: Xuehui Sun, Kennett Square, PA (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 53 days.

(21) Appl. No.: 17/267,619

(22) PCT Filed: Aug. 12, 2019

(86) PCT No.: PCT/US2019/046084
§ 371 (c)(1),
(2) Date: Feb. 10, 2021

(87) PCT Pub. No.: WO2020/036836
PCT Pub. Date: Feb. 20, 2020

(65) Prior Publication Data
US 2021/0323898 A1 Oct. 21, 2021

Related U.S. Application Data

(60) Provisional application No. 62/718,255, filed on Aug. 13, 2018.

(51) Int. Cl.
| | | |
|---|---|---|
| C07C 17/20 | (2006.01) | |
| C11D 7/50 | (2006.01) | |
| C11D 7/30 | (2006.01) | |
| C09K 5/04 | (2006.01) | |
| C09K 3/30 | (2006.01) | |
| C08J 9/14 | (2006.01) | |

(52) U.S. Cl.
CPC .......... *C07C 17/206* (2013.01); *C08J 9/146* (2013.01); *C09K 3/30* (2013.01); *C09K 5/044* (2013.01); *C11D 7/30* (2013.01); *C11D 7/5018* (2013.01); *C07C 2523/26* (2013.01); *C08J 2203/162* (2013.01); *C09K 2205/126* (2013.01); *C09K 2205/22* (2013.01)

(58) Field of Classification Search
None
See application file for complete search history.

(56) References Cited

U.S. PATENT DOCUMENTS 6,329,559 B1 * 12/2001 Sievert .................. C07C 17/206
570/166
2012/0271069 A1 10/2012 Wang et al.
2014/0005446 A1 1/2014 Imura et al.
2015/0045590 A1 2/2015 Nair et al.

FOREIGN PATENT DOCUMENTS

| GB | 1171202 A | 11/1969 |
|---|---|---|
| WO | 2008/060616 A2 | 5/2008 |
| WO | 2009/035130 A2 | 3/2009 |
| WO | 2011/162341 A1 | 12/2011 |
| WO | 2017/110851 A1 | 6/2017 |

OTHER PUBLICATIONS

PCT International Search Report and Written Opinion dated Nov. 7, 2019 for PCT International Application No. PCT/US2019/046084.

\* cited by examiner

Primary Examiner — Tanisha Diggs

(57) ABSTRACT

A method of making chlorofluorohydrocarbons including, contacting, a fluorinated hydrocarbon reagent in the vapor phase, with hydrogen chloride (HCl). The reaction is conducted in the presence of an effective amount of a catalyst, at an elevated temperature sufficient to effect hydrochlorination to form a reaction mixture including a chlorofluorohydrocarbon.

17 Claims, No Drawings

COMPOSITIONS AND PROCESSES FOR PRODUCING CHLOROFLUOROALKENES

This application claims the benefit of Application No. 62/718,255, filed on Aug. 13, 2018. The disclosure of 62/718,255 is hereby incorporated by reference.

FIELD OF THE DISCLOSURE

The present invention is directed to a method of making hydrochlorofluorocarbons. In particular, the present invention is directed to a selective process for making chlorofluoroalkenes, such as 1-chloro-2,3,3,3-tetrafluoropropene (Z/E).

BACKGROUND INFORMATION

Hydrofluorocarbons (HFCs), such as HFC-134a and HFC-245fa, have recently been used as replacements for chlorofluorocarbons (CFCs) and hydrochlorofluorocarbons (HCFCs), which can potentially damage the earth's ozone layer. Hydrofluorocarbons (HFCs) have been employed as effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. HFCs do not contribute to the destruction of stratospheric ozone, but, are of concern due to their contribution to the "greenhouse effect", i.e., they contribute to global warming. As a result of their contribution to global warming, the HFCs have come under scrutiny, and their widespread use has been restricted. Thus, there is a need for compositions that do not contribute to the destruction of stratospheric ozone and also have low global warming potentials (GWPs).

WO 2011/162341 A1 describes a gas phase process which produces HCFO-1224yd as an intermediate in a gas phase process for the production of HCFO-1234yf. The process employs hydrogen gas ($H_2$) for the hydrogenation of HCFO-1214ya in the presence of a catalyst.

WO 2017/110851 A1 describes a liquid phase process for the production of HCFO-1224yd. The process employs a basic solution, such as KOH, for the dehydrochlorination of HCFC-234bb to form 1224yd in the presence of a catalyst. The starting material, 234bb, was made by chlorination of 1234yf, which is an expensive material. The process generates large aqueous waste. The 1224yd product made from this process contains 5.5%-6.4% 1224yd(E) isomer. The 1224yd(Z) isomer is the desired product for many applications. The 1224yd(E) produced in the process needs additional processing to isomerize to the desired 1224yd(Z) isomer. The process may create significant waste that requires disposal incurring significant cost. The contents of which are hereby incorporated by reference in their entirety.

The disclosure of the previously identified WO publications is hereby incorporated by reference.

What is therefore needed is a highly selective process for the production of 1224yd(Z) that is less expensive and creates less waste.

SUMMARY

The instant invention can solve problems associated with conventional practices by providing inventive compositions and methods including selective processes for the production of 1224(yd)(Z). By "selective" it is meant to refer to a process that converts at least about 30 percent, about 35 to about 40 percent and, in some cases, greater than 40 percent of a reagent into 1224(yd)(Z).

In an embodiment, a method of making chlorofluoroalkenes including, contacting a reagent of formula (1), $$CF_xH_{(3-x)}(CF_yH_{(2-y)})_aCF_zH_{(3-z)}, \quad (1)$$

wherein x is an integer of 1, 2, 3, a is an integer of 0, 1, 2, 3, y is independently an integer of 0, 1, 2, and z is an integer of 1, 2, 3, in the vapor phase, with hydrogen chloride (HCl) in the presence of an effective amount of a catalyst, at an elevated temperature sufficient to effect hydrochlorination. The resulting reaction mixture includes a linear or branched compound of formula (2), $$CF_xH_{(3-x)}(CF_yH_{(2-y)})_{a-1}CF_mH_{(1-m)}=CCl_nF_pH_{(2-n-p)}, \quad (2)$$

wherein x is an integer of 1, 2, 3, a is an integer of 0, 1, 2, 3, y is independently an integer of 0, 1, 2, m is an integer of 0, 1, n is an integer of 1, 2, and p is an integer of 0, 1, and n+p is an integer of 1, 2.

In another embodiment, a method of making chlorofluoroalkenes including, contacting a reagent of formula (3), $$CF_xH_{(3-x)}(CF_bH_{(2-b)})_aCF_yH_{(1-y)}=CF_zH_{(2-z)}, \quad (3)$$

wherein x is an integer of 1, 2, 3, a is an integer of 0, 1, 2, 3, b is independently an integer of 0, 1, 2, y is independently an integer of 0, 1, and z is an integer of 1, 2, in the vapor phase, with hydrogen chloride (HCl) in the presence of an effective amount of a catalyst, at an elevated temperature sufficient to effect hydrochlorination. The resulting reaction mixture includes a linear or branched compound of formula (2), $$CF_xH_{(3-x)}(CF_yH_{(2-y)})_{a-1}CF_mH_{(1-m)}=CCl_nF_pH_{(2-n-p)}, \quad (2)$$

wherein x is an integer of 1, 2, 3, a is an integer of 0, 1, 2, 3, y is independently an integer of 0, 1, 2, m is an integer of 0, 1, n is an integer of 1, 2, and p is an integer of 0, 1, and n+p is an integer of 1, 2.

In another embodiment, a method of making chlorofluoroalkanes including, contacting, a reagent of formula (4), $$CF_xH_{(3-x)}(CF_yH_{(2-y)})_aCF_zH_{(3-z)}, \quad (4)$$

wherein x is an integer of 1-3, a is an integer of 0-3, y is independently an integer of 0-2, and z is an integer of 1-3, in the vapor phase with hydrogen chloride (HCl) in the presence of an effective amount of a catalyst, at an elevated temperature sufficient to effect hydrochlorination. The resulting reaction mixture includes a linear or branched compound of formula (5), $$CF_xH_{(3-x)}(CF_yH_{(2-y)})_aCCl_vF_{(z-v)}H_{(3-z)}, \quad (5)$$

wherein y is independently an integer of 0, 1, 2, v is independently an integer of 1, 2, z is an integer of 1, 2, and v is less than or equal to z.

Another embodiment relates to any combination of the foregoing embodiments wherein the reagent of formula (1) is selected from the group consisting of 1,1,1,2,3,3-hexafluoropropane (HFC-236ea), 1,1,1,2,2,3-hexafluoropropane (HFC-236cb), 1,1,1,2,3-pentafluoropropane (HFC-245eb), and combinations thereof; and wherein the compound of formula (2) is selected from the group consisting of (Z)-1-chloro-2,3,3,3-tetrafluoropropene (HCFO-1224yd(Z)), (E)-1-chloro-2,3,3,3-tetrafluoropropene (HCFO-1224yd(E)), (Z)-1-chloro-3,3,3-trifluoropropene (1233zd(Z)), and (E)-1-chloro-3,3,3-trifluoropropene (1233zd(E)).

Another embodiment relates to any combination of the foregoing embodiments wherein the compound of formula (2) includes a mixture of (Z)-1-chloro-2,3,3,3-tetrafluoropropene (HCFO-1224yd(Z)) and (E)-1-chloro-2,3,3,3-tetrafluoropropene (HCFO-1224yd(E)).

Another embodiment relates to any combination of the foregoing embodiments and further comprising, recovering the compound of formula (2) from the reaction mixture.

Another embodiment relates to any combination of the foregoing embodiments and further comprising recycling at least a portion of the (E)-1-chloro-2,3,3,3-tetrafluoropropene (HCFO-1224yd(E)) to the reaction.

Another embodiment relates to any combination of the foregoing embodiments and further comprising recycling at least a portion of 3-chloro-1,1,1,2,2-pentafluoropropane (HFC-235cb) produced back into the reaction.

Another embodiment relates to any combination of the foregoing embodiments wherein the catalyst is selected from the group consisting of chromium oxide, fluorinated chromium oxide, oxyfluorides of chrome, chromium halide, alumina, aluminum fluoride, fluorided alumina, metal compounds on aluminum fluoride, metal compounds on fluorided alumina; oxides, fluorides, and oxyfluorides of magnesium, zinc and mixtures of magnesium and zinc and/or aluminum; lanthanum oxide and fluorided lanthanum oxide; carbon, acid-washed carbon, activated carbon, three dimensional matrix carbonaceous materials; metal compounds supported on carbon and combinations thereof.

Another embodiment relates to any combination of the foregoing embodiments wherein the catalyst is aluminum oxide ($Al_2O_3$) chromium oxide ($Cr_2O_3$), zinc doped chromium oxide, or chromium oxide supported on aluminum oxide ($Al_2O_3$).

Another embodiment relates to any combination of the foregoing embodiments wherein molar ratio of hydrogen chloride to the sum of the moles of the reagents of formula (1) and the moles the compounds of formula (2) is about 0.2:1 to about 10:1.

Another embodiment relates to any combination of the foregoing embodiments wherein the elevated temperature sufficient to effect formation of the reaction mixture is between 150° C. and 500° C.

Another embodiment relates to any combination of the foregoing embodiments wherein the reagent of formula (3) is 1,2,3,3,4,4,4-heptafluoro-1-butene. (HFC-1327cye) or 1,2,3,3,3-pentafluoropropene (HFO-1225ye).

Another embodiment relates to any combination of the foregoing embodiments wherein the compound of formula (2) is (Z)-1-chloro-2,3,3,4,4,4-hexafluoro-1-butene (HCFC-1326yd(Z)), (E)-1-chloro-2,3,3,4,4,4-hexafluoro-1-butene (HCFC-1326yd(E)), (Z)-1-chloro-2,3,3,3-tetrafluoropropene (HCFO-1224yd(Z)), or (E)-1-chloro-2,3,3,3-tetrafluoropropene (HCFO-1224yd(E)).

Another embodiment relates to any combination of the foregoing embodiments wherein at least 90 percent of the reagent of formula (3) is converted to (Z)-1-chloro-2,3,3,3-tetrafluoropropene (HCFO-1224yd(Z)).

Another embodiment relates to any combination of the foregoing embodiments and further comprising:
 contacting, the compound of formula (5), in the vapor phase with a dehydrohalogenation catalyst or in the liquid phase with a caustic, at an elevated temperature sufficient to form a reaction mixture including a compound of formula (6),

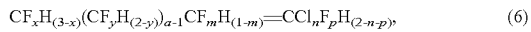
(6)

wherein x is an integer of 1, 2, 3, a is an integer of 0, 1, 2, 3, y is an integer of 0, 1, 2, y is independently 0, 1 or 2, m is an integer of 0, 1, n is an integer of 1, 2, p is an integer of 0, 1, and n+p is an integer of 1, 2.

One embodiment relates to a composition and including a composition produced by any combination of the foregoing processes.

Another embodiment relates to any combination of the foregoing embodiments wherein the composition comprises (Z)-1-chloro-2,3,3,3-tetrafluoropropene (HCFO-1224yd(Z)), (E)-1-chloro-2,3,3,3-tetrafluoropropene (HCFO-1224yd(E)), (Z)-1,2,3,3,3-pentafluoropropene (HFO-1225ye(Z)), and (E)-1,2,3,3,3-pentafluoropropene (HFO-1225ye(E)).

Another embodiment relates to any combination of the foregoing embodiments wherein the composition comprises (Z)-1-chloro-2,3,3,3-tetrafluoropropene (HCFO-1224yd(Z)), (E)-1-chloro-2,3,3,3-tetrafluoropropene (HCFO-1224yd(E)), (Z)-1,2,3,3,3-pentafluoropropene (HFO-1225ye(Z)), (E)-1,2,3,3,3-pentafluoropropene (HFO-1225ye(E)), and 1,1,1,2,3,3-hexafluoropropane (HFC-236ea).

Another embodiment relates to any combination of the foregoing embodiments wherein the composition comprises (Z)-1-chloro-2,3,3,3-tetrafluoropropene (HCFO-1224yd(Z)), (E)-1-chloro-2,3,3,3-tetrafluoropropene (HCFO-1224yd(E)), (Z)-1,2,3,3,3-pentafluoropropene (HFO-1225ye(Z)), (E)-1,2,3,3,3-pentafluoropropene (HFO-1225ye(E)), and 1,1,1,2,2,3-hexafluoropropane (HFC-236cb).

Another embodiment of the invention relates to any combination of the foregoing embodiments wherein the composition comprises (Z)-1-chloro-2,3,3,3-tetrafluoropropene (HCFO-1224yd(Z)), (E)-1-chloro-2,3,3,3-tetrafluoropropene (HCFO-1224yd(E)), (Z)-1,2,3,3,3-pentafluoropropene (HFO-1225ye(Z)), (E)-1,2,3,3,3-pentafluoropropene (HFO-1225ye(E)), 3-chloro-1,1,1,2,2-pentafluoropropane (HFC-235cb), and 1,1,1,2,2,3-hexafluoropropane (HFC-236cb).

Another embodiment of the invention relates to any combination of the foregoing embodiments wherein the composition comprises (Z)-1-chloro-2,3,3,3-tetrafluoropropene (HCFO-1224yd(Z)), (E)-1-chloro-2,3,3,3-tetrafluoropropene (HCFO-1224yd(E)), (Z)-1,2,3,3,3-pentafluoropropene (HFO-1225ye(Z)), and (E)-1,2,3,3,3-pentafluoropropene (HFO-1225ye(E)), and 3-chloro-1,1,1,2,2-pentafluoropropane (HFC-235cb).

Another embodiment of the invention relates to any combination of the foregoing embodiments wherein the composition comprises (Z)-1-chloro-3,3,3-trifluoropropene (1233zd(Z)) and (E)-1-chloro-3,3,3-trifluoropropene (1233zd(E)), and 1-chloro-2,3,3,3-tetrafluoropropane (HCFC-244eb).

Another embodiment of the invention relates to any combination of the foregoing embodiments wherein the composition comprises (Z)-1-chloro-3,3,3-trifluoropropene (1233zd(Z)) and (E)-1-chloro-3,3,3-trifluoropropene (1233zd(E)), and 1-chloro-1,3,3,3-tetrafluoropropane (HCFC-244fa).

Another embodiment of the invention relates to any combination of the foregoing embodiments wherein the composition comprises (Z)-1-chloro-3,3,3-trifluoropropene (1233zd(Z)) and (E)-1-chloro-3,3,3-trifluoropropene (1233zd(E)), and 1,1,1,3,3-pentafluoropropane (HFC-245fa).

Another embodiment of the invention relates to any combination of the foregoing embodiments wherein the composition comprises (Z)-1-chloro-3,3,3-trifluoropropene (1233zd(Z)) and (E)-1-chloro-3,3,3-trifluoropropene (1233zd(E)), and 1,1,1,2,3-pentafluoropropane (HFC-245eb).

Another embodiment of the invention relates to any combination of the foregoing embodiments wherein the composition comprises (Z)-1-chloro-3,3,3-trifluoropropene (1233zd(Z)) and (E)-1-chloro-3,3,3-trifluoropropene (1233zd(E)), and 1,1,2-trichloro-2,3,3,3-tetrafluoropropane (HCFC-224ba).

Another embodiment of the invention relates to any combination of the foregoing embodiments wherein the composition comprises (Z)-1-chloro-2,3,3,3-tetrafluoropropene (HCFO-1224yd(Z)), (E)-1-chloro-2,3,3,3-tetrafluoropropene (HCFO-1224yd(E)), (Z)-1,2,3,3,3-pentafluoropropene (HFO-1225ye(Z)), (E)-1,2,3,3,3-pentafluoropropene (HFO-1225ye(E)), (Z)-1,2-dichloro-3,3,3-trifluoropropene (1223xd(Z)), and (E)-1,2-dichloro-3,3,3-trifluoropropene (1223xd(E)).

Another embodiment of the invention relates to any combination of the foregoing embodiments wherein the composition comprises (Z)-1-chloro-2,3,3,3-tetrafluoropropene (HCFO-1224yd(Z)), (E)-1-chloro-2,3,3,3-tetrafluoropropene (HCFO-1224yd(E)), (Z)-1,2,3,3,3-pentafluoropropene (HFO-1225ye(Z)), (E)-1,2,3,3,3-pentafluoropropene (HFO-1225ye(E)), and 1,1,1,2,2,3-hexafluoropropane (HFC-236cb).

Another embodiment of the invention relates to any combination of the foregoing embodiments wherein the composition comprises (Z)-1-chloro-3,3,3-trifluoropropene (1233zd(Z)), (E)-1-chloro-3,3,3-trifluoropropene (1233zd(E)), and 1,1,1,3,3-pentafluoropropane (HFC-245fa).

Another embodiment of the invention relates to any combination of the foregoing embodiments wherein the composition comprises 1,1,1,2,2,3-heptafluoropropane (HFC-236cb), 3-chloro-1,1,1,2,2-pentafluoropropane (HFC-235cb), (Z)-1-chloro-2,3,3,3-tetrafluoropropene (HCFO-1224yd(Z)), and (E)-1-chloro-2,3,3,3-tetrafluoropropene (HCFO-1224yd(E)).

Another embodiment of the invention relates to any combination of the foregoing embodiments wherein the composition comprises 1,3,3,3-tetrafluoropropene (HFC-1234ze), (Z)-1-chloro-3,3,3-trifluoropropene (1233zd(Z)), (E)-1-chloro-3,3,3-trifluoropropene (1233zd(E)), 1-chloro-2,3,3,3-tetrafluoropropane (HCFC-244eb), and 1,1,1,2,3-pentafluoropropane (HFC-245eb).

The embodiments of the invention can be used alone or in combinations with each other. Other features and advantages of the present invention will be apparent from the following more detailed description, taken in conjunction with the accompanying drawings which illustrate, by way of example, the principles of the invention.

DETAILED DESCRIPTION

The present invention provides a vapor phase process for the hydrochlorination of chlorofluoroalkanes, fluorinated alkanes and fluorinated alkenes to form chloroalkanes, chlorofluoroalkanes, chlorofluoroalkenes, and chloroalkenes. The present invention further provides for the conversion of chlorofluoroalkane to chlorofluoroalkenes.

The present invention additionally provides compounds, such as 1-chloro-2,3,3,3-tetrafluoropropene (1224yd), which are useful as cleaning agents, refrigerants, blowing agents, solvents, and aerosols with low global warming potential (GWP).

In an embodiment, a reagent of formula (1), $$CF_xH_{(3-x)}(CF_yH_{(2-y)})_aCF_zH_{(3-z)}, \quad (1)$$

wherein x is an integer of 1, 2, 3, a is an integer of 0, 1, 2, 3, y is independently an integer of 0, 1, 2, and z is an integer of 1, 2, 3, in the vapor phase with hydrogen chloride (HCl) in the presence of an effective amount of a catalyst, at an elevated temperature sufficient to effect hydrochlorination. The resulting reaction mixture includes a linear or branched hydrochlorinated compound of formula (2), $$CF_xH_{(3-x)}(CF_yH_{(2-y)})_{a-1}CF_mH_{(1-m)}=CCl_nF_pH_{(2-n-p)}, \quad (2)$$

wherein x is an integer of 1, 2, 3, a is an integer of 0, 1, 2, 3, y is independently an integer of 0, 1, 2, m is an integer of 0, 1, n is an integer of 1, 2, and p is an integer of 0, 1, and n+p is an integer of 1, 2.

In an embodiment, a reagent of formula (3), $$CF_xH_{(3-x)}(CF_bH_{(2-b)})_aCF_yH_{(1-y)}=CF_zH_{(2-z)}, \quad (3)$$

wherein x is an integer of 1, 2, 3, a is an integer of 0, 1, 2, 3, b is independently an integer of 0, 1, 2, y is independently an integer of 0, 1, and z is an integer of 1, 2, is contacted in the vapor phase, with hydrogen chloride (HCl) in the presence of an effective amount of a catalyst, at an elevated temperature sufficient to effect hydrochlorination. The resulting reaction mixture includes a linear or branched hydrochlorinated compound of formula (2), $$CF_xH_{(3-x)}(CF_yH_{(2-y)})_{a-1}CF_mH_{(1-m)}=CCl_nF_pH_{(2-n-p)}, \quad (2)$$

wherein x is an integer of 1, 2, 3, a is an integer of 0, 1, 2, 3, y is independently an integer of 0, 1, 2, m is an integer of 0, 1, n is an integer of 1, 2, and p is an integer of 0, 1, and n+p is an integer of 1, 2.

In an embodiment, a reagent of formula (4), $$CF_xH_{(3-x)}(CF_yH_{(2-y)})_aCF_zH_{(3-z)}, \quad (4)$$

wherein x is an integer of 1, 2, 3, a is an integer of 0, 1, 2, 3, y is an integer of 0, 1, 2, and z is an integer of 1, 2, 3, is contacted in the vapor phase with hydrogen chloride (HCl) in the presence of an effective amount of a catalyst, at an elevated temperature sufficient to effect hydrochlorination. The resulting reaction mixture includes a linear or branched hydrochlorinated compound of formula (5), $$CF_xH_{(3-x)}(CF_yH_{(2-y)})_aCCl_vF_{(z-v)}H_{(3-z)}, \quad (5)$$

wherein x is an integer of 1, 2, 3, a is an integer of 0, 1, 2, 3, y is independently an integer of 0, 1, 2, v is an integer of 1, 2, z is an integer of 1, 2, and v is less than or equal to z.

In an embodiment, a reagent of formula (5), $$CF_xH_{(3-x)}(CF_yH_{(2-y)})_aCCl_vF_{(z-v)}H_{(3-z)}, \quad (5)$$

wherein x is an integer of 1, 2, 3, a is an integer of 0, 1, 2, 3, y is independently an integer of 0, 1, 2, v is an integer of 1, 2, z is an integer of 1, 2, and v is less than or equal to z, is contacted in the vapor phase with a dehydrohalogenation catalyst or contacted in the liquid phase with a caustic. The resulting reaction mixture includes compound of formula (6), $$CF_xH_{(3-x)}(CF_yH_{(2-y)})_{a-1}CF_mH_{(1-m)}=CCl_nF_pH_{(2-n-p)}, \quad (6)$$

wherein x is an integer of 1, 2, 3, a is an integer of 0, 1, 2, 3, y is an integer of 0, 1, 2, y is independently 0, 1 or 2, m is an integer of 0, 1, n is an integer of 1, 2, p is an integer of 0, 1, and n+p is an integer of 1, 2.

An embodiment includes, a vapor phase process for the conversion of 1,2,3,3,3-pentafluoropropene (HFO-1225ye) into 1-chloro-2,3,3,3-tetrafluoropropene(Z/E) (HCFO-1224yd(Z/E)). HCFO-1224yd(Z/E) is produced in a highly selective process yielding predominately HCFO-1224yd(Z). HCFO-1224yd as used herein refers to the isomers, HCFO-1224yd(E) or HCFO-1224yd(Z), as well as any combinations or mixtures of such isomers. The conversion of 1,2,3, 3,3-pentafluoropropene (HFO-1225ye) into 1-chloro-2,3,3,3-tetrafluoropropene(Z/E) (HCFO-1224yd(Z/E)) is shown in scheme (7).

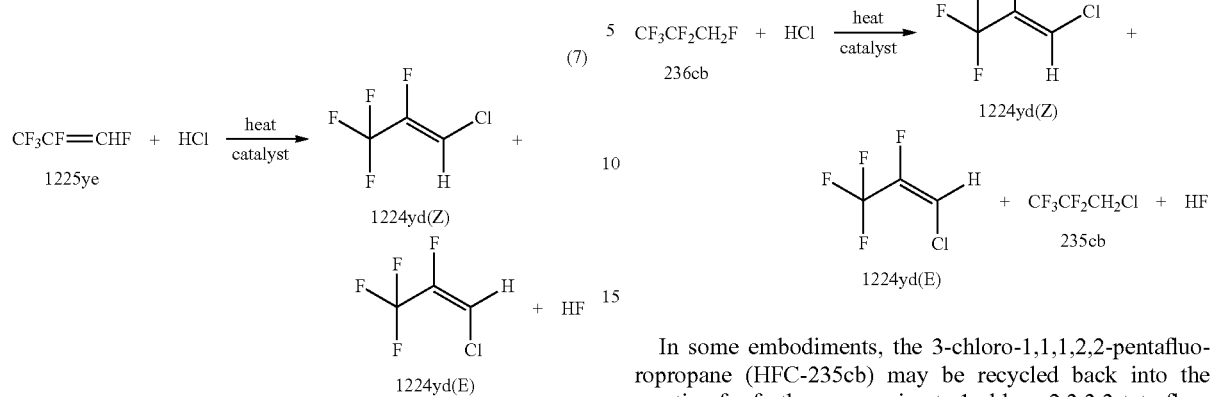

An embodiment includes, a vapor phase process for the conversion of 1,1,1,2,3,3-hexafluoropropane (HFC-236ea) into 1-chloro-2,3,3,3-tetrafluoropropene(Z/E) (HCFO-1224yd(Z/E)). HCFO-1224yd(Z/E) is produced in a highly selective process yielding predominately HCFO-1224yd(Z). HCFO-1224yd as used herein refers to the isomers, HCFO-1224yd(E) or HCFO-1224yd(Z), as well as any combinations or mixtures of such isomers. The conversion of 1,1,1,2,3,3-hexafluoropropane (HFC-236ea) into 1-chloro-2,3,3,3-tetrafluoropropene(Z/E) (HCFO-1224yd(Z/E)) is shown in scheme (8).

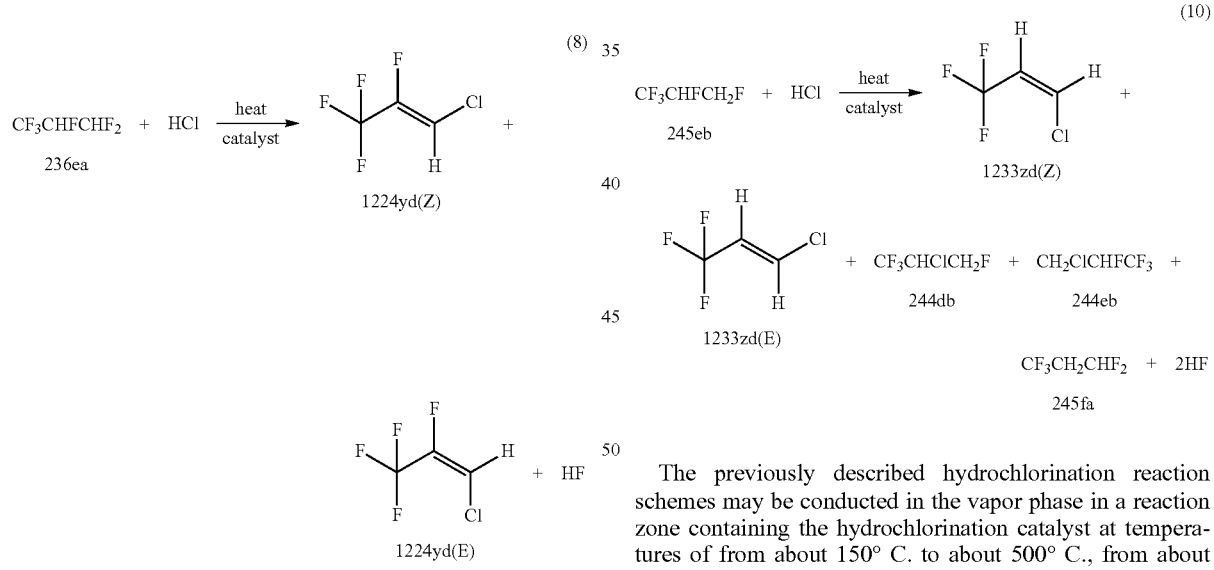

An embodiment includes, a vapor phase process for the conversion of 1,1,1,2,2,3-hexafluoropropane (HFC-236cb) into 1-chloro-2,3,3,3-tetrafluoropropene(Z/E) (HCFO-1224yd(Z/E)). HCFO-1224yd(Z/E) is produced in a highly selective process yielding predominately HCFO-1224yd(Z). HCFO-1224yd as used herein refers to the isomers, HCFO-1224yd(E) or HCFO-1224yd(Z), as well as any combinations or mixtures of such isomers. The conversion of 1,1,1,2,2,3-hexafluoropropane (HFC-236cb) into 1-chloro-2,3,3,3-tetrafluoropropene(Z/E) (HCFO-1224yd(Z/E)) is shown in scheme (9).

In some embodiments, the 3-chloro-1,1,1,2,2-pentafluoropropane (HFC-235cb) may be recycled back into the reaction for further conversion to 1-chloro-2,3,3,3-tetrafluoropropene(Z/E) (HCFO-1224yd(Z/E)). In some embodiments, the 3-chloro-1,1,1,2,2-pentafluoropropane (HFC-235cb) may be converted to 1-chloro-2,3,3,3-tetrafluoropropene(Z/E) (HCFO-1224yd(Z/E)) by reacting with a caustic or by dehydrofluorinating over a dehydrofluorination catalyst.

An embodiment includes, a vapor phase process for the conversion of 1,1,1,2,3-pentafluoropropane (HFC-245eb) into 1-chloro-3,3,3-trifluoropropene (1233zd) by a hydrochlorination reaction. The reaction is shown below as scheme (10).

The previously described hydrochlorination reaction schemes may be conducted in the vapor phase in a reaction zone containing the hydrochlorination catalyst at temperatures of from about 150° C. to about 500° C., from about 175° C. to about 400° C., from about 200° C. to about 350° C., and/or from about 200° C. to about 300° C. The contact time is typically from about 1 to about 450 seconds and/or from about 10 to about 120 seconds.

In some embodiments, a hydrochlorination catalyst suitable for use in the foregoing reaction schemes includes a vapor phase chrome or to aluminum oxide catalyst. In an embodiment, the hydrochlorination catalyst includes aluminum oxide ($Al_2O_3$). In an embodiment, the hydrochlorination catalyst includes chromium oxide ($Cr_2O_3$). In an embodiment, the hydrochlorination catalyst includes chromium oxide supported on aluminum oxide. In an embodiment, the hydrochlorination catalyst includes zinc doped chromium oxide. Suitable catalysts include, but are not limited to, chromium oxide, fluorinated chromium oxide, oxyfluorides of chrome, chromium halide, alumina, aluminum fluoride, fluorided alumina, metal compounds on aluminum fluoride, metal compounds on fluorided alumina; oxides, fluorides, and oxyfluorides of magnesium, zinc and mixtures of magnesium and zinc and/or aluminum; lanthanum oxide and fluorided lanthanum oxide; carbon, acid-washed carbon, activated carbon, three dimensional matrix carbonaceous materials; and metal compounds supported on carbon. The metal compounds are oxides, fluorides, and oxyfluorides of at least one metal selected from the group consisting of sodium, potassium, rubidium, cesium, yttrium, lanthanum, cerium, praseodymium, neodymium, samarium, chromium, iron, cobalt, rhodium, nickel, copper, zinc, and mixtures thereof. The catalyst is contacted for a time sufficient to affect the desired reaction scheme.

The reaction pressure used in the foregoing reaction schemes can be sub-atmospheric, atmospheric or super-atmospheric. In one embodiment, the hydrochlorination is performed at super-atmospheric pressures (i.e., pressures greater than one atmosphere). In one embodiment, the hydrochlorination is performed at substantially atmospheric pressure. In some embodiments, the reaction may be performed at a pressure of 0-100, 0-50, 0-30, 1-25, 5-20, or 7-15 pounds per square inch gauged (psig).

The molar ratio of hydrogen chloride to the organic components of the reaction mixture used in the foregoing reaction schemes may be between about 0.2:1 to about 10:1, about 0.3:1 to about 5:1, or about 0.4:1 to about 2:1.

The catalytic hydrochlorination of the foregoing reaction schemes may optionally include additional gases. The addition of one or more additional gases can be used to increase the lifetime of the catalyst. In some embodiments, the mole fraction of the additional gas based on the total gas is from about 0.1 mole percent to about 3 mole percent, about 0.2 mole percent to about 2 mole percent, about 0.5 mole percent to about 1.5 mole percent, about 1 mole percent to about 1.5 mole percent, about 1.5 mole percent to about 2 mole percent, about 2 mole percent to about 3 mole percent, or about 2.2 mole percent to about 2.5 mole percent. In one embodiment, the additional gas includes oxygen ($O_2$).

The additional gases used in the foregoing reaction schemes may include one or more inert gases. In some embodiments, the reaction is performed under nitrogen, helium, and/or argon. In some embodiments, the gases used as the reactor atmosphere may be pre-dried to remove substantially all water. In one embodiment, the reaction is performed under dry nitrogen.

The effluent from the reaction zone of the vapor-phase fluorination reactor typically includes one or more of HCl, HF, HCFO-1224yd, HCFC-235cb, HFC-236ea, HFC-236cb, 1223xd, and HFO-1225ye.

The desired HCFO-1224yd(Z), and mixtures thereof with HF, may be separated from the reaction mixture by methods known in the art (e.g., distillation). The catalyst used for the hydrochlorination reaction is also typically a suitable catalyst for the isomerization of HCFO-1224yd(Z) to HCFO-1224yd(E) and/or HCFO-1224yd(E) to HCFO-1224yd(Z). In order to maintain the concentration of HCFO-1224yd(E) at or in excess of the equilibrium concentration, HCFO-1224yd(E) may be fed back into the reaction to reach or exceed the equilibrium concentration between the isomers thereby suppressing further formation of HCFO-1224yd(E), thus favoring the desired HCFO-1224yd(Z) isomer. In some embodiments, a portion of the HCFO-1224yd(E) may be isomerized to HCFO-1224yd(Z) by feeding back the HCFO-1224yd(E) into the reaction to cause the concentration of HCFO-1224yd(E) to exceed the equilibrium concentration. In some embodiments, this results in an overall selectivity of the HCFO-1224yd(Z) isomer of greater than 90 percent, greater than 92 percent, greater than 95 percent, and/or greater than 97 percent.

In some embodiments, the intermediates, such as HCFC-235cb, and unreacted HFO-1225ye may be fed back into the reaction to increase the overall yield. In some embodiments, the overall conversion of HFO-1225ye into HCFO-1224yd (Z) may be greater than 80 percent, greater than 85 percent, and/or greater than 90 percent.

In one embodiment, the inventive process can produce a composition comprising about 7 to about 95 percent and, in some cases, about 40 to about 90 percent HCFO-1224(yd)(Z), and the remainder comprising at least one additional compound selected from the group consisting of 1225ye(Z), 1225ye(E) and 236cb. The additional compounds having a lower boiling point than HCFO-1224(yd)(Z) and can impart improved refrigeration performance.

The reactor, distillation columns, and their associated feed lines, effluent lines, and associated units used in applying the process of this invention should be constructed of materials resistant to hydrogen fluoride and hydrogen chloride. Typical materials of construction, well-known to the fluorination art, include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

In alternate embodiments, 1,1,1,2,3,3-hexafluoropropane (HFC-236ea) and/or 1,1,1,2,2,3-hexafluoropropane (HFC-236cb) may be substituted for or used in combination with the 1,2,3,3,3-pentafluoropropene (HFO-1225ye) as the starting reagent for the production of HCFO-1224yd.

The following Examples are provided to illustrate certain embodiments of the invention and shall not limit the scope of the appended claims.

EXAMPLES

Example 1

Hydrochlorination of HFO-1225ye to 1224yd by Chrome Oxide Catalyst JM 62-3

8 ml 12-20 mesh Johnson Matthey chrome oxide catalyst was loaded into a ½ inch Hastelloy C 227 reactor. The catalyst was dried at 250° C. for 2 hours and then activated by HF treatment at a temperature of from 300° C. to 425° C. Then HCl and HFO-1225ye was fed into the reactor at atmosphere pressure. The conditions of reaction are listed in Table 1 below. The stream from the reactor was analyzed by GC and GC-MS. The results of the test are also shown in Table 1. The higher conversion of HFO-1225ye and good yield of 1224yd were made in this reaction.

TABLE 1

HFO-1225ye hydrochlorination reaction

| Example | Reactor temp ° C. | 1225ye sccm | HCl sccm | HCl/1225ye mol ratio | 1225ye conversion | 1224yd selectivity |
|---|---|---|---|---|---|---|
| 1.1 | 200 | 3.01 | 9.43 | 3.13 | 95.0% | 97.4% |
| 1.2 | 225 | 3.07 | 9.45 | 3.13 | 79.0% | 98.3% |
| 1.3 | 250 | 3.01 | 9.43 | 3.13 | 99.9% | 92.1% |
| 1.4 | 300 | 3.01 | 9.43 | 3.13 | 99.8% | 72.8% |
| 1.5 | 325 | 3.01 | 9.43 | 3.13 | 100.0% | 70.6% |
| 1.6 | 350 | 3.01 | 9.43 | 3.13 | 99.7% | 71.3% |
| 1.7 | 140 | 6.06 | 9.22 | 1.52 | 7.7% | 93.4% |
| 1.8 | 160 | 6.32 | 9.47 | 1.50 | 13.8% | 96.1% |
| 1.9 | 180 | 6.35 | 9.49 | 1.49 | 25.2% | 97.7% |
| 1.10 | 200 | 6.32 | 9.49 | 1.50 | 43.2% | 98.4% |
| 1.11 | 140 | 8.65 | 9.46 | 1.09 | 6.2% | 93.4% |
| 1.12 | 160 | 8.91 | 9.48 | 1.06 | 11.3% | 96.3% |
| 1.13 | 180 | 8.98 | 9.49 | 1.06 | 19.9% | 97.8% |
| 1.14 | 200 | 8.63 | 9.49 | 1.10 | 33.6% | 98.4% |

Mole Percents

| Example | 1225ye-Z | 1225ye-E | 236ea | 1224yd-Z | 1224yd-E | 1223xd | 233da | 235da | others |
|---|---|---|---|---|---|---|---|---|---|
| 1.1 | 4.50% | 0.46% | 0.21% | 89.53% | 3.02% | 0.69% | 0.42% | 0.00% | 1.18% |
| 1.2 | 18.92% | 2.09% | 0.00% | 74.78% | 2.88% | 0.21% | 0.23% | 0.15% | 0.73% |
| 1.3 | 0.10% | 0.01% | 0.00% | 88.05% | 3.99% | 6.21% | 0.39% | 0.00% | 1.26% |
| 1.4 | 0.16% | 0.02% | 0.23% | 66.80% | 5.85% | 24.71% | 1.06% | 0.00% | 1.16% |
| 1.5 | 0.00% | 0.03% | 0.00% | 64.59% | 5.96% | 26.14% | 1.26% | 0.00% | 2.02% |
| 1.6 | 0.25% | 0.04% | 0.00% | 65.23% | 5.83% | 25.06% | 1.33% | 0.00% | 2.26% |
| 1.7 | 89.21% | 3.05% | 0.00% | 7.03% | 0.19% | 0.00% | 0.03% | 0.15% | 0.33% |
| 1.8 | 83.02% | 3.22% | 0.00% | 12.85% | 0.37% | 0.00% | 0.05% | 0.15% | 0.34% |
| 1.9 | 71.30% | 3.52% | 0.00% | 23.87% | 0.73% | 0.00% | 0.09% | 0.16% | 0.34% |
| 1.10 | 53.15% | 3.61% | 0.07% | 41.19% | 1.36% | 0.05% | 0.13% | 0.17% | 0.27% |
| 1.11 | 90.80% | 2.96% | 0.00% | 5.67% | 0.15% | 0.00% | 0.02% | 0.11% | 0.28% |
| 1.12 | 85.54% | 3.14% | 0.00% | 10.59% | 0.30% | 0.00% | 0.03% | 0.12% | 0.27% |
| 1.13 | 76.63% | 3.42% | 0.00% | 18.93% | 0.58% | 0.00% | 0.05% | 0.12% | 0.27% |
| 1.14 | 62.62% | 3.77% | 0.07% | 32.01% | 1.08% | 0.00% | 0.08% | 0.13% | 0.24% |

Example 2

Hydrochlorination of 236ea to 1224yd by Chrome Oxide Catalyst JM 62-3

8 ml 12-20 mesh Johnson Matthey chrome oxide catalyst was loaded into a ½ inch Hastelloy C 227 reactor. The catalyst was dried at 250° C. for 2 hours and then activated by HF treatment at a temperature of from 300° C. to 425° C. Then HCl and 236ea was fed into the reactor at atmosphere pressure. The conditions of reaction are listed in Table 2 below. The stream from the reactor was analyzed by GC and GC-MS. The results of the test are also shown in Table 2. The higher conversion of 236ea and good yield of 1224yd were made in this reaction.

TABLE 2

236ea hydrochlorination reaction

| Example | Reactor Temp ° C. | 236ea cc/hr | N2 sccm | NCl sccm | HCl/236ea mol ratio | 236ea conversion | 1224yd selectivity |
|---|---|---|---|---|---|---|---|
| 2.1 | 180 | 1.5 | 0.0 | 10.4 | 1.83 | 5.80% | 0.90% |
| 2.2 | 200 | 1.5 | 0.0 | 10.4 | 1.83 | 7.50% | 2.60% |
| 2.3 | 225 | 1.5 | 0.0 | 10.4 | 1.83 | 26.20% | 10.60% |
| 2.4 | 250 | 1.5 | 0.0 | 10.4 | 1.83 | 54.00% | 59.10% |
| 2.5 | 275 | 1.5 | 0.0 | 10.4 | 1.83 | 85.80% | 82.70% |
| 2.6 | 250 | 1.5 | 5.0 | 5.5 | 0.96 | 50.40% | 87.40% |
| 2.7 | 250 | 2.0 | 5.0 | 5.5 | 0.72 | 43.20% | 89.00% |

Mole Percents

| Example | 1225ye-Z | 1225ye-E | 236ea | 1224yd-Z | 1224yd-E | 235da | 1223xd | 224ba | Others |
|---|---|---|---|---|---|---|---|---|---|
| 2.1 | 0.01% | 0.00% | 94.19% | 0.04% | 0.01% | 0.94% | 0.00% | 0.66% | 4.15% |
| 2.2 | 0.01% | 0.00% | 92.54% | 0.17% | 0.03% | 1.63% | 0.00% | 3.50% | 2.12% |
| 2.3 | 0.01% | 0.00% | 73.77% | 2.52% | 0.27% | 2.29% | 0.44% | 17.70% | 3.01% |
| 2.4 | 0.05% | 0.01% | 46.05% | 30.07% | 1.83% | 2.85% | 6.09% | 10.00% | 3.06% |
| 2.5 | 0.22% | 0.03% | 14.22% | 67.32% | 3.60% | 0.72% | 11.86% | 1.26% | 0.77% |

TABLE 2-continued

| | | | 236ea hydrochlorination reaction | | | | | | |
|---|---|---|---|---|---|---|---|---|---|
| 2.6 | 0.29% | 0.04% | 49.61% | 41.89% | 2.14% | 0.59% | 3.53% | 0.63% | 1.30% |
| 2.7 | 0.38% | 0.05% | 56.78% | 36.63% | 1.85% | 0.78% | 2.40% | 0.35% | 0.78% |

Example 3

Hydrochlorination of 245eb by Chrome Oxide Catalyst JM 62-3

After reaction with 236ea in example 1 was done, the reactor was purged with N2 to remove the organic from 236ea reaction. Then HCl and 245eb was fed into the reactor at atmosphere pressure. The conditions of reaction are listed in Table 3 below. The stream from the reactor was analyzed by GC and GC-MS. The results of the test are also shown in Table 3.

TABLE 3

| | 245eb hydrochlorination reaction | | | | |
|---|---|---|---|---|---|
| Example | Reactor temp °C. | 245eb cc/hr | N2 sccm | NCl sccm | HCl/245eb mol ratio |
| 3.1 | 250 | 1.50 | 40 | 5.51 | 0.9 |
| 3.2 | 250 | 3.00 | 35 | 5.51 | 0.4 |
| 3.3 | 275 | 1.51 | 40 | 5.51 | 0.9 |
| 3.4 | 275 | 3.00 | 35 | 5.51 | 0.4 |
| 3.5 | 300 | 1.51 | 40 | 5.51 | 0.9 |
| 3.6 | 300 | 3.00 | 35 | 5.51 | 0.4 |
| 3.7 | 160 | 1.51 | 40 | 5.51 | 0.9 |
| 3.8 | 160 | 3.00 | 35 | 5.51 | 0.4 |
| 3.9 | 180 | 1.51 | 40 | 5.51 | 0.9 |
| 3.10 | 180 | 3.00 | 35 | 5.51 | 0.4 |
| 3.11 | 200 | 1.51 | 40 | 5.51 | 0.9 |
| 3.12 | 200 | 3.00 | 35 | 5.51 | 0.4 |
| 3.13 | 225 | 1.51 | 40 | 5.51 | 0.9 |
| 3.14 | 225 | 3.00 | 35 | 5.51 | 0.4 |

| | Mole Percents | | | | | | |
|---|---|---|---|---|---|---|---|
| Example | 1234 | 245cb | 1234ze | 1234ze | 245eb | 245fa | 244fa |
| 3.1 | 22.205% | 1.48% | 0.22% | 3.83% | 0.30% | 65.12% | 3.04% |
| 3.2 | 50.746% | 1.57% | 0.21% | 9.62% | 0.18% | 30.94% | 0.61% |
| 3.3 | 9.276% | 10.92% | 1.73% | 0.33% | 2.11% | 0.19% | 69.13% |
| 3.4 | 26.719% | 26.80% | 2.59% | 0.00% | 4.10% | 0.13% | 36.81% |
| 3.5 | 22.116% | 2.61% | 0.47% | 1.14% | 0.10% | 67.21% | 5.33% |
| 3.6 | 31.260% | 22.15% | 3.64% | 0.00% | 0.00% | 2.51% | 0.07% |
| 3.7 | 0.299% | 0.00% | 0.00% | 0.00% | 24.56% | 0.00% | 0.00% |
| 3.8 | 0.000% | 0.00% | 0.00% | 0.00% | 57.60% | 0.00% | 0.00% |
| 3.9 | 0.821% | 0.00% | 0.01% | 0.00% | 11.61% | 11.40% | 0.00% |
| 3.10 | 1.454% | 0.00% | 0.01% | 0.00% | 56.88% | 0.00% | 0.05% |
| 3.11 | 2.454% | 0.00% | 0.05% | 0.00% | 12.37% | 12.15% | 0.01% |
| 3.12 | 5.528% | 0.00% | 0.07% | 0.01% | 51.61% | 0.00% | 0.05% |
| 3.13 | 7.851% | 0.00% | 0.34% | 0.05% | 9.06% | 0.00% | 0.08% |
| 3.14 | 17.545% | 0.00% | 0.33% | 0.04% | 37.23% | 0.00% | 0.07% |

| | Mole Percents | | | | | | |
|---|---|---|---|---|---|---|---|
| Example | 1233xf | 1233zd-E | 1233zd-Z | 244db | 244eb | 243db | Others |
| 3.1 | 0.30% | 0.22% | 2.50% | 0.74% | 0.00% | 0.00% | 0.05% |
| 3.2 | 0.00% | 0.55% | 5.23% | 0.32% | 0.00% | 0.00% | 0.03% |
| 3.3 | 4.71% | 0.59% | 0.00% | 0.78% | 0.19% | 0.00% | 0.07% |
| 3.4 | 1.34% | 0.21% | 0.00% | 0.68% | 0.05% | 0.00% | 0.57% |
| 3.5 | 0.72% | 0.00% | 0.18% | 0.04% | 0.00% | 0.00% | 0.08% |
| 3.6 | 37.30% | 1.76% | 0.25% | 0.00% | 0.18% | 0.01% | 0.87% |
| 3.7 | 0.03% | 0.03% | 0.03% | 0.20% | 74.46% | 0.39% | 0.00% |
| 3.8 | 0.03% | 0.03% | 0.00% | 0.14% | 41.79% | 0.06% | 0.34% |
| 3.9 | 0.25% | 0.23% | 0.11% | 0.57% | 73.70% | 1.29% | 0.00% |
| 3.10 | 0.15% | 0.14% | 0.05% | 0.53% | 40.59% | 0.14% | 0.00% |
| 3.11 | 1.87% | 1.75% | 0.29% | 1.39% | 64.95% | 2.70% | 0.00% |
| 3.12 | 1.05% | 0.98% | 0.15% | 1.22% | 38.93% | 0.41% | 0.00% |
| 3.13 | 14.98% | 14.01% | 0.00% | 2.00% | 45.58% | 6.04% | 0.00% |
| 3.14 | 5.91% | 5.53% | 0.00% | 1.75% | 30.76% | 0.85% | 0.00% |

Example 4

Hydrochlorination of 236ea to 1224yd by BASF 4126 Al2O3

2 ml 12-20 mesh BASF 4126 Al2O3 catalyst was loaded into a ½ inch Hastelloy C 227 reactor. The catalyst was dried at 250° C. for 2 hours and then activated by HF treatment at a temperature of from 300° C. to 425° C. Then HCl and 236ea was fed into the reactor at atmosphere pressure. The conditions of reaction are listed in Table 3 below. The stream from the reactor was analyzed by GC and GC-MS. The results of the test are also shown in Table 4. The 1224yd were made in this reaction.

TABLE 4

| | 236ea hydrochlorination reaction | | | | | | |
|---|---|---|---|---|---|---|---|
| Example | Reactor temp °C. | 236ea cc/hr | N2 sccm | NCl sccm | HCl/236ea mol ratio | 236ea conversion | 1224yd selectivity |
| 4.1 | 250 | 6.00 | 40 | 5.5 | 0.24 | 2.6% | 54.90% |
| 4.2 | 250 | 3.00 | 45 | 5.5 | 0.48 | 3.0% | 61.60% |
| 4.3 | 275 | 6.00 | 40 | 5.5 | 0.24 | 5.5% | 51.80% |
| 4.4 | 275 | 3.00 | 45 | 5.5 | 0.48 | 6.4% | 64.30% |
| 4.5 | 300 | 6.00 | 40 | 5.5 | 0.24 | 10.2% | 48.10% |
| 4.6 | 300 | 3.00 | 45 | 5.5 | 0.48 | 14.1% | 59.40% |
| 4.7 | 250 | 6.00 | 20 | 5.6 | 0.25 | 2.2% | 42.30% |
| 4.8 | 250 | 3.00 | 25 | 5.6 | 0.49 | 2.3% | 42.40% |
| 4.9 | 275 | 6.00 | 20 | 5.6 | 0.25 | 3.0% | 39.60% |
| 4.10 | 275 | 3.00 | 25 | 5.6 | 0.49 | 2.9% | 41.40% |

TABLE 4-continued

| | | | 236ea hydrochlorination reaction | | | | |
|---|---|---|---|---|---|---|---|
| 4.11 | 300 | 6.00 | 20 | 5.6 | 0.25 | 4.5% | 36.10% |
| 4.12 | 300 | 3.00 | 25 | 5.6 | 0.49 | 6.4% | 43.80% |

| | Mole Percents | | | | | | | |
|---|---|---|---|---|---|---|---|---|
| Example | 1225ye-Z | 1225ye-E | 236ea | 1224yd-Z | 1224yd-E | 235da | 1223xd | Others |
| 4.1 | 0.95% | 0.12% | 97.40% | 1.35% | 0.08% | 0.02% | 0.03% | 0.06% |
| 4.2 | 0.86% | 0.11% | 97.01% | 1.73% | 0.11% | 0.03% | 0.05% | 0.10% |
| 4.3 | 2.18% | 0.30% | 94.48% | 2.69% | 0.17% | 0.04% | 0.05% | 0.10% |
| 4.4 | 1.79% | 0.24% | 93.64% | 3.84% | 0.25% | 0.05% | 0.08% | 0.11% |
| 4.5 | 4.40% | 0.66% | 89.83% | 4.56% | 0.33% | 0.04% | 0.07% | 0.11% |
| 4.6 | 4.70% | 0.71% | 85.86% | 7.85% | 0.55% | 0.05% | 0.14% | 0.13% |
| 4.7 | 0.28% | 0.05% | 97.79% | 0.91% | 0.02% | 0.00% | 0.00% | 0.94% |
| 4.8 | 0.30% | 0.05% | 97.74% | 0.92% | 0.04% | 0.02% | 0.01% | 0.92% |
| 4.9 | 0.71% | 0.10% | 97.05% | 1.12% | 0.04% | 0.02% | 0.02% | 0.93% |
| 4.10 | 0.62% | 0.09% | 97.11% | 1.15% | 0.05% | 0.02% | 0.04% | 0.92% |
| 4.11 | 1.53% | 0.23% | 95.54% | 1.53% | 0.08% | 0.02% | 0.04% | 1.04% |
| 4.12 | 2.04% | 0.31% | 93.63% | 2.63% | 0.16% | 0.03% | 0.11% | 1.10% |

Example 5

Hydrochlorination of 236cb to 235cb and HCFO-1224yd by Chrome Oxide Catalyst JM 62-3

2 ml 12-20 mesh Johnson Matthey chrome oxide catalyst was loaded into a ½ inch Hastelloy C 227 reactor. The catalyst was dried at 250° C. for 2 hours and then activated by HF treatment from 300° C. to 425° C. Then HCl and 236cb was fed into the reactor at atmosphere pressure. The conditions of reaction are listed in Table 2 below. The stream from the reactor was analyzed by GC and GC-MS. The results of the test are also shown in Table 5. The higher conversion of 236cb and good yield of 235cb and 1224yd were made in this reaction.

TABLE 5

| | 236cb hydrochlorination reaction | | | | | | | | |
|---|---|---|---|---|---|---|---|---|---|
| Example | Reactor temp ° C. | 236cb cc/hr | N2 sccm | NCl sccm | HCl/236cb mol ratio | 236cb conversion | 1224yd selectivity | 235cb selectivity | 1224yd + 235cb selectivity |
| 5.1 | 250 | 1.50 | 14.98 | 5.5 | 1.0 | 71.3% | 0.2% | 99.5% | 99.7% |
| 5.2 | 250 | 1.50 | 10.01 | 5.5 | 1.0 | 70.2% | 0.3% | 99.6% | 99.9% |
| 5.3 | 250 | 3.00 | 5.00 | 5.5 | 0.5 | 48.1% | 0.1% | 99.6% | 99.7% |
| 5.4 | 275 | 1.51 | 9.97 | 5.5 | 1.0 | 89.8% | 1.7% | 98.7% | 100.3% |
| 5.5 | 275 | 3.00 | 5.08 | 5.5 | 0.5 | 55.8% | 0.7% | 98.5% | 99.2% |
| 5.6 | 300 | 1.51 | 9.63 | 5.5 | 1.0 | 89.9% | 5.7% | 93.3% | 99.0% |
| 5.7 | 300 | 3.00 | 4.99 | 5.5 | 0.5 | 52.5% | 5.6% | 93.5% | 99.2% |
| 5.8 | 275 | 1.50 | 0.00 | 5.6 | 1.0 | 88.5% | 1.2% | 98.5% | 99.7% |
| 5.9 | 300 | 1.50 | 0.00 | 5.6 | 1.0 | 90.8% | 5.9% | 93.2% | 99.2% |
| 5.10 | 325 | 1.50 | 0.00 | 5.6 | 1.0 | 88.2% | 23.1% | 73.4% | 96.6% |
| 5.11 | 350 | 1.50 | 0.00 | 5.6 | 1.0 | 85.4% | 50.5% | 40.3% | 90.8% |

| | Mole Percents | | | | | | | | |
|---|---|---|---|---|---|---|---|---|---|
| Example | 1225ye-Z | 236cb | 1225ye-E | 236ea | 1224xe | 1224yd-Z | 235cb | 235da | 1223xd | others |
| 5.1 | 0.00% | 28.65% | 0.00% | 0.00% | 0.00% | 0.15% | 71.00% | 0.00% | 0.03% | 0.17% |
| 5.2 | 0.00% | 29.85% | 0.00% | 0.00% | 0.00% | 0.13% | 69.90% | 0.00% | 0.02% | 0.11% |
| 5.3 | 0.00% | 51.93% | 0.00% | 0.00% | 0.00% | 0.07% | 47.90% | 0.00% | 0.00% | 0.09% |
| 5.4 | 0.00% | 10.24% | 0.00% | 0.00% | 0.00% | 0.93% | 88.58% | 0.00% | 0.11% | 0.14% |
| 5.5 | 0.00% | 44.23% | 0.00% | 0.00% | 0.01% | 0.69% | 54.92% | 0.00% | 0.02% | 0.13% |
| 5.6 | 0.00% | 10.10% | 0.00% | 0.00% | 0.06% | 5.28% | 83.84% | 0.00% | 0.47% | 0.25% |
| 5.7 | 0.00% | 47.47% | 0.00% | 0.00% | 0.08% | 2.98% | 49.13% | 0.00% | 0.08% | 0.25% |
| 5.8 | 0.00% | 11.48% | 0.00% | 0.00% | 0.00% | 1.08% | 87.18% | 0.00% | 0.10% | 0.16% |
| 5.9 | 0.00% | 9.15% | 0.08% | 0.00% | 0.05% | 5.27% | 84.70% | 0.00% | 0.46% | 0.27% |
| 5.10 | 0.00% | 11.82% | 0.26% | 0.39% | 0.31% | 20.17% | 64.76% | 0.16% | 1.77% | 0.35% |
| 5.11 | 0.00% | 14.56% | 0.78% | 1.07% | 1.18% | 43.32% | 34.42% | 0.18% | 3.87% | 0.62% |

What is claimed is:

1. A method of making chlorofluoroalkenes comprising: contacting, a reagent of formula (1),

wherein x is an integer of 1, 2, 3, a is an integer of 0, 1, 2, 3, y is independently an integer of 0, 1, 2, and z is an integer of 1, 2, 3 comprising one of 1,1,1,2,3,3-hexafluoropropane (HFC-236ea), 1,1,1,2,2,3-hexafluoropropane (HFC-236cb), 1,1,1,2,3-pentafluoropropane (HFC-245eb), and combinations thereof, in the vapor phase, with hydrogen chloride (HCl) in the presence of a catalyst, at an elevated temperature sufficient to effect hydrochlorination to form a reaction mixture including compounds of formula (2),

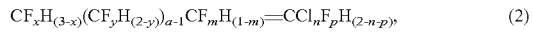

wherein x is an integer of 1, 2, 3, a is an integer of 0, 1, 2, 3, y is independently an integer of 0, 1, 2, m is an integer of 0, 1, n is an integer of 1, 2, and p is an integer of 0, 1, and n+p is an integer of 1, 2, wherein the reaction mixture comprises at least a mixture of (Z)-1-chloro-2,3,3,3-tetrafluoropropene (HCFO-1224yd(Z)) and (E)-1-chloro-2,3,3,3-tetrafluoropropene (HCFO-1224yd(E).

2. The method of claim 1 further comprising, recovering the compounds of formula (2) from the reaction mixture.

3. The method of claim 1 further comprising recycling at least a portion of the (E)-1-chloro-2,3,3,3-tetrafluoropropene (HCFO-1224yd(E)) to the reaction.

4. The method of claim 1 further comprising recycling at least a portion of 3-chloro-1,1,1,2,2-pentafluoropropane (HFC-235cb) produced back into the reaction.

5. The method of claim 1, wherein the catalyst is selected from the group consisting of chromium oxide, fluorinated chromium oxide, oxyfluorides of chrome, chromium halide, alumina, aluminum fluoride, fluorided alumina, metal compounds on aluminum fluoride, metal compounds on fluorided alumina;

oxides, fluorides, and oxyfluorides of magnesium, zinc and mixtures of magnesium and zinc and/or aluminum; lanthanum oxide and fluorided lanthanum oxide; carbon, acid-washed carbon, activated carbon, three dimensional matrix carbonaceous materials; metal compounds supported on carbon and combinations thereof.

6. The method of claim 5, wherein the catalyst is aluminum oxide ($Al_2O_3$) chromium oxide ($Cr_2O_3$), zinc doped chromium oxide, or chromium oxide supported on aluminum oxide ($Al_2O_3$).

7. The method of claim 1, wherein molar ratio of hydrogen chloride to the sum of the moles of the reagents of formula (1) and the moles the compounds of formula (2) is about 0.2:1 to about 10:1.

8. The method of claim 1, wherein the elevated temperature sufficient to effect formation of the reaction mixture is between 150° C. and 500° C.

9. A method of making chlorofluoroalkenes comprising: contacting, a reagent of formula (3),

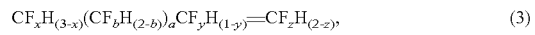

wherein x is an integer of 1, 2, 3, a is an integer of 0, 1, 2, 3, b is independently an integer of 0, 1, 2, y is independently an integer of 0, 1, and z is an integer of 1, 2, which comprises one of 1,2,3,3,4,4,4-heptafluoro-1-butene, (HFC-1327cye) and 1,2,3,3,3-pentafluoropropene (HFO-1225ye), in the vapor phase, with hydrogen chloride (HCl) in the presence of a catalyst, at an elevated temperature sufficient to effect hydrochlorination to form a reaction mixture including a compound of formula (2),

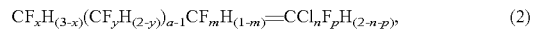

wherein x is an integer of 1, 2, 3, a is an integer of 0, 1, 2, 3, y is independently an integer of 0, 1, 2, m is an integer of 0, 1, n is an integer of 1, 2, and p is an integer of 0, 1, and n+p is an integer of 1, 2.

10. The method of claim 9, wherein the compound of formula (2) is (Z)-1-chloro-2,3,3,4,4,4-hexafluoro-1-butene (HCFC-1326yd(Z)), (E)-1-chloro-2,3,3,4,4,4-hexafluoro-1-butene (HCFC-1326yd(E)), (Z)-1-chloro-2,3,3,3-tetrafluoropropene (HCFO-1224yd(Z)), or (E)-1-chloro-2,3,3,3-tetrafluoropropene (HCFO-1224yd(E)).

11. The method of claim 9, wherein the catalyst is selected from the group consisting of chromium oxide, fluorinated chromium oxide, oxyfluorides of chrome, chromium halide, alumina, aluminum fluoride, fluorided alumina, metal compounds on aluminum fluoride, metal compounds on fluorided alumina; oxides, fluorides, and oxyfluorides of magnesium, zinc and mixtures of magnesium and zinc and/or aluminum; lanthanum oxide and fluorided lanthanum oxide; carbon, acid-washed carbon, activated carbon, three dimensional matrix carbonaceous materials; metal compounds supported on carbon and combinations thereof.

12. The method of claim 11, wherein the catalyst includes aluminum oxide ($Al_2O_3$) chromium oxide ($Cr_2O_3$), zinc doped chromium oxide, or chromium supported on aluminum oxide ($Al_2O_3$).

13. The method of claim 9, wherein the elevated temperature sufficient to effect formation of reaction mixture is between 150° C. and 500° C.

14. The method of claim 9, wherein molar ratio of hydrogen chloride to the sum of the moles of the reagents of formula (3) and the moles the compounds of formula (2) is about 0.2:1 to about 10:1.

15. The method of claim 9, wherein at least 90 percent of the reagent of formula (3) is converted to (Z)-1-chloro-2,3,3,3-tetrafluoropropene (HCFO-1224yd(Z)).

16. A method of making chlorofluoroalkanes comprising: contacting, a reagent of formula (4),

wherein x is an integer of 1, 2, 3, a is an integer of 0, 1, 2, 3, y is an integer of 0, 1, 2, and z is an integer of 1, 2, 3, in the vapor phase with hydrogen chloride (HCl) in the presence of a catalyst, at an elevated temperature sufficient to effect hydrochlorination to form a reaction mixture including a compound of formula (5), $$CF_xH_{(3-x)}(CF_yH_{(2-y)})_aCCl_vF_{(z-v)}H_{(3-z)}, \quad (5)$$

wherein x is an integer of 1, 2, 3, a is an integer of 0, 1, 2, 3, y is independently an integer of 0, 1, 2, v is an integer of 1, 2, z is an integer of 1, 2, and v is less than or equal to z, and the reaction mixture includes at least (Z)-1-chloro-2,3,3,3-tetrafluoropropene (HCFO-1224yd(Z)) and (E)-1-chloro-2,3,3,3-tetrafluoropropene (HCFO-1224yd(E) or (Z)-1-chloro-3,3,3-trifluoropropene (1233zd(Z)) and (E)-1-chloro-3,3,3-trifluoropropene (1233zd(E).

17. The method of claim 16, further comprising:
contacting, the compound of formula (5), in the vapor phase with a dehydrohalogenation catalyst or in the liquid phase with a caustic, at an elevated temperature sufficient to form a reaction mixture including a compound of formula (6), $$CF_xH_{(3-x)}(CF_yH_{(2-y)})_{a-1}CF_mH_{(1-m)}=CCl_nF_pH_{(2-n-p)}, \quad (6)$$

wherein x is an integer of 1, 2, 3, a is an integer of 0, 1, 2, 3, y is an integer of 0, 1, 2, y is independently 0, 1 or 2, m is an integer of 0, 1, n is an integer of 1, 2, p is an integer of 0, 1, and n+p is an integer of 1, 2.

* * * * *

UNITED STATES PATENT AND TRADEMARK OFFICE
CERTIFICATE OF CORRECTION

| | | |
|---|---|---|
| PATENT NO. | : 11,565,987 B2 | |
| APPLICATION NO. | : 17/267619 | |
| DATED | : January 31, 2023 | |
| INVENTOR(S) | : Xuehui Sun | |

It is certified that error appears in the above-identified patent and that said Letters Patent is hereby corrected as shown below:

In the Specification

Column 2,
After the formula (2) at about Line 14, the definition of "a is an integer of 0, 1, 2," should read
-- k is an integer of 1, 2, --;
After the formula (2) at about Line 32, the definition of "a is an integer of 0, 1, 2," should read
-- k is an integer of 1, 2, --.

Column 3,
After the formula (2) at about Line 64, the definition of "a is an integer of 0, 1, 2," should read -- k is an integer of 1, 2, --.

Column 6,
After the formula (2) at Line 7, the definition of "a is an integer of 0, 1, 2," should read -- k is an integer of 1, 2, --;
After the formula (2) at Line 24, the definition of "a is an integer of 0, 1, 2," should read -- k is an integer of 1, 2, --;
After the formula (2) at Line 55, the definition of "a is an integer of 0, 1, 2," should read -- k is an integer of 1, 2, --.

In the Claims

Column 17, Claim 1, Line 35, after the formula (2) cancel "wherein x is an integer of 1, 2, 3, a is an integer of 0,1," and insert -- wherein x is an integer of 1, 2, 3, k is an integer of 1, --.

Column 18, Claim 9, Line 25, after the formula (2) cancel "wherein x is an integer of 1, 2, 3, a is an integer of 0,1," and insert -- wherein x is an integer of 1, 2, 3, k is an integer of 1, --.

Column 19, Claim 17, Line 21, after the formula (6) cancel "wherein x is an integer of 1, 2, 3, a is an integer of 0, 1," and insert -- wherein x is an integer of 1, 2, 3, k is an integer of 1, --.

Signed and Sealed this
Ninth Day of May, 2023

*Katherine Kelly Vidal*
Katherine Kelly Vidal
*Director of the United States Patent and Trademark Office*